United States Patent
Pyo

(10) Patent No.: US 6,409,679 B2
(45) Date of Patent: Jun. 25, 2002

(54) APPARATUS AND METHOD FOR COLLECTING BODILY FLUID

(75) Inventor: Richard Sung Hak Pyo, Irvine, CA (US)

(73) Assignee: Pacific Paragon Investment Fund Ltd., Vancouver (CA)

( * ) Notice: Subject to any disclaimer, the term of this patent is extended or adjusted under 35 U.S.C. 154(b) by 0 days.

(21) Appl. No.: 09/879,729

(22) Filed: Jun. 12, 2001

Related U.S. Application Data

(60) Provisional application No. 60/211,204, filed on Jun. 13, 2000.

(51) Int. Cl.[7] .................................................. A61B 5/00
(52) U.S. Cl. ...................................... 600/573; 604/313
(58) Field of Search ................................ 600/567, 573; 604/128, 129, 313, 315, 316

(56) References Cited

U.S. PATENT DOCUMENTS

| | | | | |
|---|---|---|---|---|
| 3,786,801 A | * | 1/1974 | Sartorius | .................... 600/573 |
| 4,542,751 A | * | 9/1985 | Webster et al. | ............. 600/573 |
| 4,844,098 A | * | 7/1989 | Mitchen | ..................... 128/765 |
| 5,417,206 A | * | 5/1995 | Kaneyoshi | ................. 128/632 |
| 5,762,640 A | * | 6/1998 | Kajiwara et al. | ........... 600/573 |
| 6,045,541 A | * | 4/2000 | Matsumoto et al. | ........ 600/573 |

* cited by examiner

Primary Examiner—Max Hindenburg
(74) Attorney, Agent, or Firm—Jerry H. Noh

(57) ABSTRACT

An apparatus for drawing bodily fluid from a person comprising a suction module having a hole extending from its top surface to its bottom surface. A removeable lid covers the hole at the top surface. The bottom surface of the module adheres to the skin of the individual. A bore extends from the outer surface of the module into the hole, and a pumping mechanism attaches to the bore to creating a vacuum within said hole by drawing air out of said module. As a vacuum is created, skin is drawn into the hole to form a blister containing bodily fluids within the hole. The blister having bodily fluid therein is ruptured, and its fluid content is collected.

14 Claims, 2 Drawing Sheets

APPARATUS AND METHOD FOR COLLECTING BODILY FLUID

RELATED APPLICATION

This application claims the benefit of Provisional Patent Application No. 60/211,204 filed Jun. 13, 2000. The entire contents of this provisional patent application are incorporated by reference herein.

BACKGROUND OF THE INVENTION

I. Field of The Invention

This invention pertains to an apparatus and a method of collecting bodily fluids from individuals. More specifically, the invention concerns an apparatus and a minimal to non-invasive method of collecting bodily fluids from individuals by inducing a suction blister and collecting the fluids accumulated therein.

II. Description of the Prior Art

The common conventional method of extracting bodily fluid from an individual utilizes a lancet or a needle to puncture the skin deep enough to allow the desired amount of fluid such as blood to be collected. Diabetics, typically must have periodic extractions of blood to measure for glucose. For diabetics, the fingertip is pricked with a needle and the same fingertip is squeezed to draw the necessary amount of blood. The blood is then placed on a test strip to analyze the glucose content. Often if the sample of blood collected is too small, the fingertip must be punctured again until enough blood is collected. A disadvantage with this conventional method is the pain involved in puncturing the skin especially in the area of the fingertip. The fingertip area is sensitive in that it contains a high concentration of nerve endings.

Another method and apparatus for extracting bodily fluid is taught in U.S. Pat. No. 5,879,310 issued to Sopp et al. According to the method in Sopp, a needle portion of a body fluid collection apparatus is protruded into an individual until it penetrates into a body fluid-laden skin layer. A sampler carried within the apparatus has an absorbent medium in fluid flow communication with the needle for body fluid to flow from the needle onto the medium. The disadvantages of such a method and apparatus is the pain involved in penetration with the needle and also the relatively high cost of such a device.

Thus, a system which allows bodily fluids to be extracted with very little or no pain is desirable.

SUMMARY OF THE INVENTION

It is a primary objective of the present invention to provide a minimal to non-invasive method and apparatus for extracting bodily fluids with the least amount of pain. It is yet another objective of the present invention to provide an apparatus for extracting bodily fluids which is relatively easy and inexpensive to manufacture.

The present invention provides a system which allows bodily fluid to be drawn not necessarily from the fingers as pricking a finger is known to be painful because of the high nerve ending concentration at the fingers. Instead the present invention allows bodily fluid to be drawn in a minimal to non-invasive manner from less painful areas of the body including the forearm, thigh, and upper arm.

In the present invention, bodily fluid is drawn using a suction module which has a hole extending from its top surface to its bottom surface. The bottom surface of the module adheres to the skin of the individual, and skin is drawn into the hole to form a blister by creating negative pressure within the hole. The blister containing bodily fluid therein is ruptured, and its fluid content is collected using a chemically treated testing strip which draws up fluid via capillary action. The testing strip containing the fluid is then tested to examine the fluid content. The fluid contained in the blister is usually interstitial fluid, and sometimes the fluid also contains blood. It is desirable to form blister containing only interstitial fluid.

The present invention is effective in testing for blood glucose level in diabetics using the interstitial fluid collected from the blister.

BRIEF DESCRIPTION OF THE DRAWING

With the above and additional objects and advantages in view, as will hereinafter appear, this invention comprises the devices, combinations and arrangements of parts hereinafter described, by way of example, and illustrated in the accompanying drawings of a preferred embodiment in which.

DESCRIPTION OF THE PREFERRED EMBODIMENT

Figure 4:
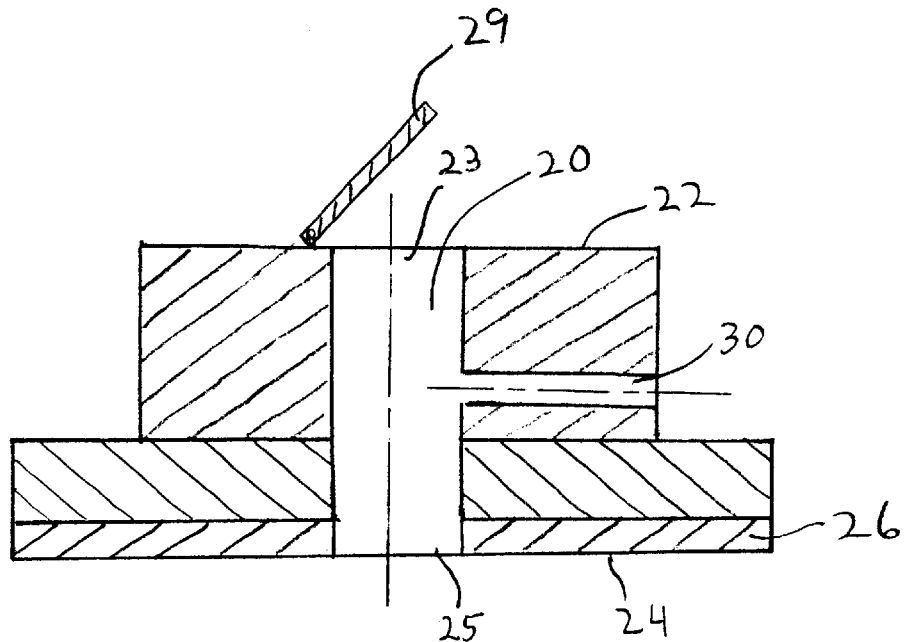
FIG. 4 is a side cross-sectional view of the apparatus of the present invention.

FIGS. 1–4 shows the preferred embodiment of the apparatus of the present invention. The apparatus is a suction module 10 being substantially cylindrical in shape. The lower edge 15 of the module 10 has a base 18 extending radially for a predetermined radius. The module 10 defines a central primary hole 20 which extends from the top surface 22 to the bottom surface 24. The primary hole 20 defines a first opening 23 at the top surface 22 and a second opening 25 at the bottom surface 24 of the module 10. The bottom surface 24 of the module 10 has a layer of an adhesive material 26 which causes the module 10 to adhere to an individual's skin. The adhesive material 26 is of the type known in the art which allows an airtight seal to form between the skin and the module 10.

Figure 1:
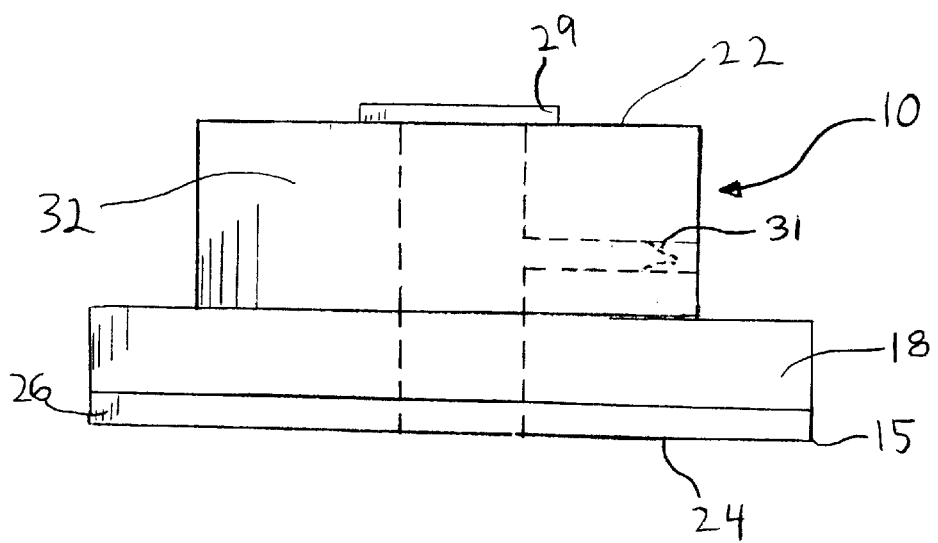
FIG. 1 is a side view of the apparatus of the present invention.
Figure 3:
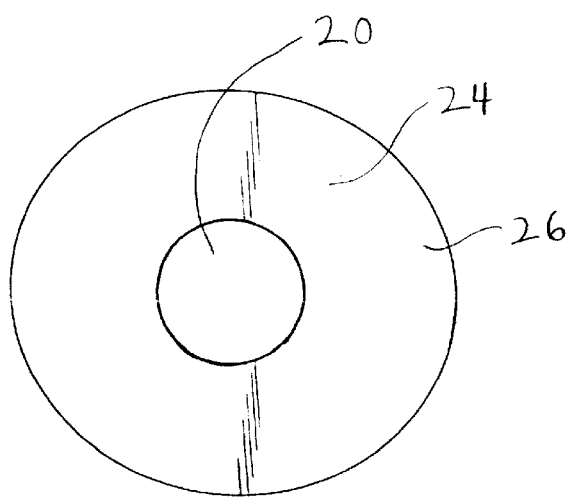
FIG. 3 is a bottom plan view of the apparatus of the present invention.
Figure 2:
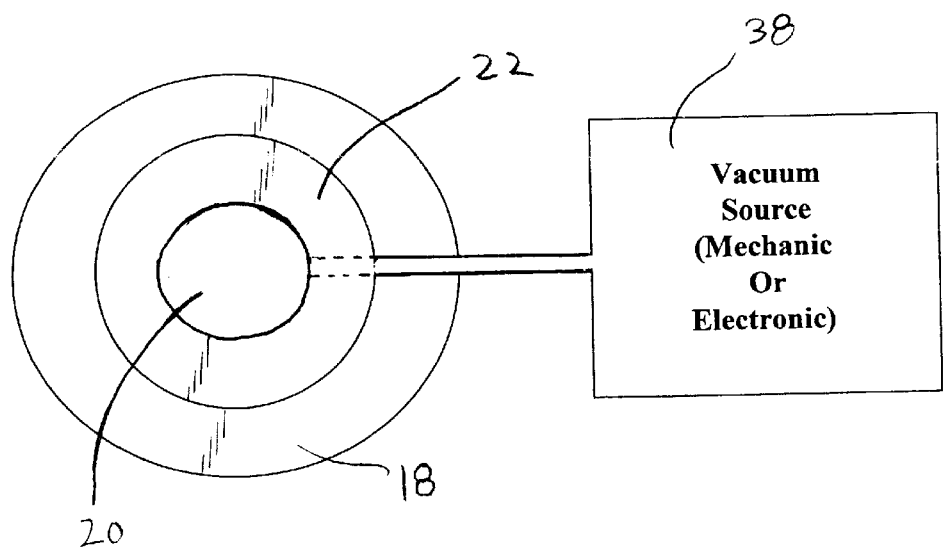
FIG. 2 is a top plan view of the apparatus of the present invention.

The module 10 further comprises a removeable lid 29 covering the first opening 23 at the top surface 22 of the module 10. Also, a bore 30 extends from the side surface 32 of the module 10 into the primary hole 20. A one way valve 31 as illustrated in FIG. 1 is placed within the second opening 30 which allows air to flow only out from within the primary hole 20. The module 10 operates in conjunction with a separate electric or manual pump mechanism 38 and a chemically treated testing strip (not shown) which draws up fluid via capillary action.

In order to draw bodily fluid, first the module 10 is placed on the arm of the individual. The adhesive material 26 causes the module 10 to tightly engage the skin. The lid 29 should be covering the first opening 23 at the top surface 22 in an airtight manner. Next, the pumping mechanism 38 which attaches to the side surface 32 over the second opening 30 is activated to create negative pressure within the primary hole 20 and bore 30 by sucking out air. The vacuum created within the hole 20 and bore 30 pull upon the individual's skin, thereby inducing a suction blister as skin is sucked into the hole 20. The negative pressure necessary for the vacuum to create the blister is approximately 200 mmHg.

The blister created by the vacuum contains interstitial fluid and sometimes blood. The fluid in the blister is collected by removing the lid 29 and inserting a testing strip which has a pointed end for rupturing the blister with only minimal application of pressure. Once the blister is ruptured with the testing strip, the fluid is released into the hole 20 and the testing strip absorbs the fluid via capillary action. The testing strip containing the fluid is then tested with the corresponding monitoring meter to examine the fluid content. The testing strip can be completely separate from the monitoring meter and later placed into the meter, as is done in traditional methods. In the alternative, the testing strip can be attached as part of the monitoring meter and the testing strip while attached to the meter is placed into the hole 20 defined by the module 10 when collecting fluid.

In the alternative, prior to attaching the module 10 onto an individual's arm, the area in which the module 10 will be attached is first wiped with a predetermined solution which loosens the skin and opens the pores. One predetermined solution known in the art to produce such an effect on skin is Pilocarpine solution. There are other solutions known in the art which performs such functions and may be substituted in place of Pilocarpine solution. The application of the solution can improve the formation of the blister with the module 10 and also can simplify the collection of the interstitial fluid in that the blister will rupture with the application very little pressure using the testing strip or on its own.

While a preferred embodiment of the invention has been described and illustrated for purposes of clarity and example, it should be understood that many changes, substitutions and modifications to the described embodiment will be apparent to those having skill in the art in light of the foregoing disclosure without departing from the scope and spirit of the present invention.

What is claimed is:

1. An apparatus for external application onto a skin of a user, said apparatus comprising:
    a module having a top surface and a bottom surface, said module defining a primary hole extending from said top surface to said lower surface, said hole defining a first opening at said top surface and a second opening at said bottom surface;
    said module further having a lower edge and an outer surface;
    a base member extending radially for a predetermined radius from said lower edge of said module;
    a removeable lid disposed on said top surface of said module covering said first opening; and,
    a bore extending from said outer surface of said module into said primary hole;
    wherein said bottom surface of said module is placed on the surface of the skin of said user and a skin blister is created into said primary hole by creating a vacuum within said primary hole by drawing air out through said bore.

2. An apparatus as described in claim 1 further comprising a layer of adhesive material disposed on said bottom surface of said module.

3. An apparatus as described in claim 1 wherein said module is substantially cylindrical.

4. An apparatus as described in claim 1 further comprising a manual pumping mechanism attaching to said bore for creating negative pressure within said primary hole by drawing air out of said primary hole.

5. An apparatus as described in claim 1 further comprising an electric pumping mechanism attaching to said bore for creating negative pressure within said primary hole by drawing air out of said primary hole.

6. An apparatus as described in claim 1 further comprising a unidirectional valve placed within said bore which allows air to flow only out from within said primary hole.

7. An apparatus for external application onto a skin of a user, said apparatus comprising:
    a module having a top surface and a bottom surface, said module defining a primary hole extending from said top surface to said lower surface, said hole defining a first opening at said top surface and a second opening at said bottom surface;
    said module further having a lower edge and an outer surface;
    a base member extending radially for a predetermined radius from said lower edge of said module;
    a removeable lid disposed on said top surface of said module covering said first opening;
    a bore extending from said outer surface of said module into said primary hole;
    a layer of adhesive material disposed on said bottom surface of said module; and,
    a pump mechanism removeably connecting to said bore for creating negative pressure within said primary hole by drawing air out from within said primary hole;
    wherein said bottom surface of said module is placed on the surface of the skin of said user and a skin blister is created into said primary hole by activating said pump mechanism.

8. An apparatus as described in claim 7 wherein said pump mechanism is a manual pump.

9. An apparatus as described in claim 7 wherein said module is substantially cylindrical.

10. An apparatus as described in claim 7 wherein said pump mechanism is an electrical pump.

11. An apparatus as described in claim 7 further comprising a unidirectional valve placed within said bore which allows air to flow only out from within said primary hole.

12. A method of collecting bodily fluid from the skin of a person using a suction module having a top surface and a bottom surface, said module defining a primary hole extending from said top surface to said lower surface, said hole defining a first opening at said top surface, said module further having a removeable lid disposed on said top surface of said module covering said first opening, said method comprising the steps of:
    placing said bottom surface of said module on said surface of the skin of said person;
    inducing the formation of a skin blister within said primary hole by creating a vacuum within said primary hole;
    removing said lid of said module;
    rupturing said blister formed within said primary hole; and,
    collecting said bodily fluid discharged from said blister.

13. A method as described in claim 12 further comprising the step of applying a predetermined solution which loosens the skin and opens the pores on said surface of said skin prior to placing said module on said skin.

14. A method as described in claim 12 wherein said bodily fluid is collected using a testing strip which absorbs the fluid via capillary action.

* * * * *